United States Patent [19]

Yanagisawa et al.

[11] Patent Number: 4,740,837

[45] Date of Patent: Apr. 26, 1988

[54] ENDOSCOPE APPARATUS WITH SOLID STATE IMAGE PICKUP DEVICE

[75] Inventors: Takuji Yanagisawa, Chigasaki; Yuuichi Muranaka, Ootawara, both of Japan

[73] Assignee: Kabushiki Kaisha Toshiba, Kawasaki, Japan

[21] Appl. No.: 909,040

[22] Filed: Sep. 19, 1986

[30] Foreign Application Priority Data

Sep. 19, 1985 [JP] Japan .................................. 60-207157
Feb. 28, 1986 [JP] Japan .................................. 61-43675

[51] Int. Cl.$^4$ .......................... H04N 7/18; H04N 5/30
[52] U.S. Cl. ...................................... 358/98; 358/209; 128/4; 128/6
[58] Field of Search .......................... 358/98, 909, 209; 128/4, 6

[56] References Cited

U.S. PATENT DOCUMENTS

| | | | |
|---|---|---|---|
| Re. 31,290 | 6/1983 | Moore et al. ............... | 358/98 |
| 4,524,761 | 6/1985 | Hattori et al. ............. | 128/6 |
| 4,622,584 | 11/1986 | Nagasaki et al. ........... | 358/98 |
| 4,625,714 | 12/1986 | Toyota et al. ............. | 358/98 |
| 4,646,724 | 3/1987 | Sato et al. ................ | 128/6 |

Primary Examiner—James J. Groody
Assistant Examiner—John K. Peng
Attorney, Agent, or Firm—Finnegan, Henderson, Farabow, Garrett & Dunner

[57] ABSTRACT

An endoscope apparatus includes a solid-state image pickup device, a memory, a display, and an illumination system. The solid-state image pickup device is mounted at the distal end of an insertion portion to be inserted in a body cavity and picks up an image of the body cavity. The image pickup device forms a one-frame image by a plurality of fields. The memory stores the one-frame image formed from an image signal of succeeding fields obtained from the image pickup device. The display displays the image stored in the memory. The illumination system illuminates an object portion for the image pickup device with at least one light pulse in units of fields. The illumination system sets radiation phases of the light pulses in the first and last ones of the major fields constituting the one-frame image to be close to each other.

9 Claims, 7 Drawing Sheets

ENDOSCOPE APPARATUS WITH SOLID STATE IMAGE PICKUP DEVICE

BACKGROUND OF THE INVENTION

The present invention relates to an endoscope apparatus using a solid-state image pickup device which is inserted in a body cavity to pick up an image thereof.

A typical conventional endoscope apparatus uses a fiberscope having an image guide with a bundle of optical fibers. In order to display an image obtained by such an endoscope on a TV monitor and use it for a medical diagnosis, an image at an eyepiece of the fiberscope is picked up by a TV camera and displayed on the TV monitor.

An improved conventional endoscope has been proposed along with the development of a very compact solid-state image pickup device in recent years. In such an endoscope, the solid-state image pickup device is mounted in the distal end of an insertion portion of the endoscope, and an image of an object to be examined is directly picked up and extracted as a video signal without using an image guide fiber. The extracted video signal is displayed as an image on a TV monitor. Image observation and medical diagnosis according to this apparatus are performed through the TV monitor.

Figure 1:
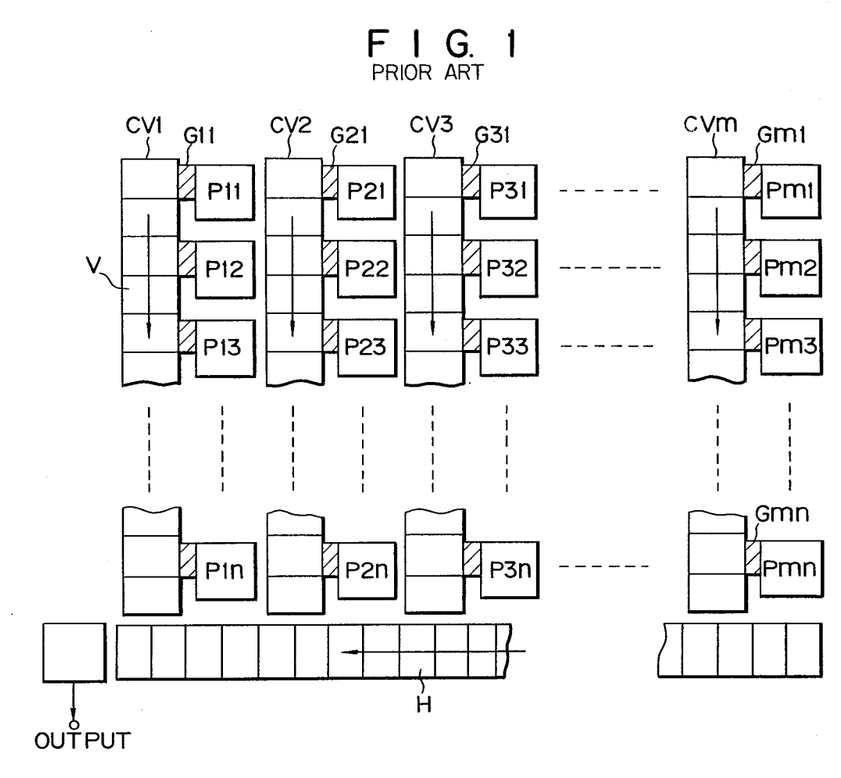
FIG. 1 is a schematic view for explaining an example of a CCD solid-state image pickup device.

A typical example of a conventional solid-state image pickup device is shown in FIG. 1.

Referring to FIG. 1, the solid-state image pickup device comprises independent light-receiving portions P11, ... Pmn, vertical transfer portions CV1, ... CVm, gates G11, ... Gmn, and horizontal transfer portion H. Upon reception of light on light-receiving portions P11, ... Pmn, signal components charged by light-receiving portions P11, ... Pmn during a field or frame period are transferred to vertical transfer portions VC1, ... VCm through gates G11, ... Gmn. When signal transfer is completed, new signal charging is started. The transferred charges are sequentially sent to horizontal transfer portion H and extracted outside the image pickup device according to a TV (scanning) scheme. Since the charges are stored in light-receiving portions P11, ... Pmn of the image pickup device according to the intensity of incident light, a portion of an object to be examined need not be illuminated by continuous light but can be by light pulses.

Figure 2A:
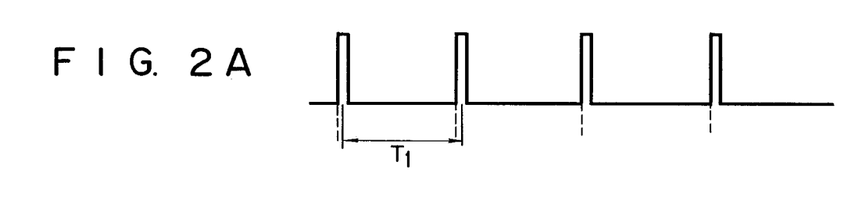
FIGS. 2A to 2C are timing charts for explaining the illumination timings of light pulses according to conventional interlaced scanning and interlaced scanning of the present invention.
Figure 2B:
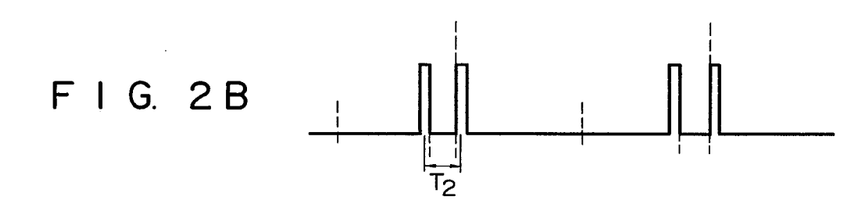
Figure 2C:
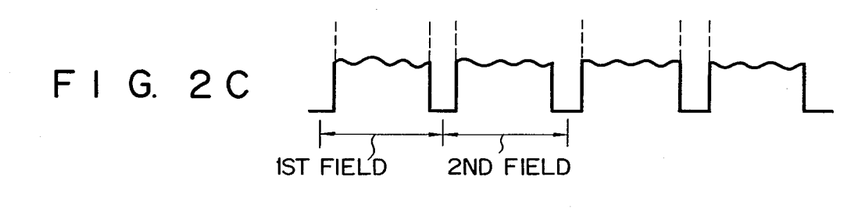

Illumination of an object portion according to the conventional apparatus is performed, as indicated by an illuminated light waveform and a video signal waveform in FIGS. 2A and 2C. Light pulses are respectively generated at start timings of the fields. An optical charge stored by the light-receiving portions during each field period is transferred to the vertical transfer portions during the transfer period within the blanking period and is then extracted as a video output through the horizontal transfer portion during the next field period.

In the case of extracting signals from the solid-state image pickup device according to interlaced scanning, signals are simultaneously extracted from the vertically adjacent light-receiving portions and are added to each other to increase signal-to-noise ratio (S/N). More specifically, the signals each generated by adding the charges from two light-receiving portions vertically aligned are simultaneously transferred to a vertical transfer portion. In this case, even if the number of light-receiving portions corresponds to a total number of pixels of one frame, signals are extracted from the light-receiving portions in units of fields and thus the storage period is one field period (normally 1/60 sec). The solid-state image pickup device having the light-receiving portions whose storage period is one field period is known as a field storage mode solid-state image pickup device.

Diagnosis and therapy using an endoscope are performed such that a doctor observes an image on a real-time basis. An image may be photographed to perform an objective diagnosis and to check an effect of the treatment.

In an endoscope using a fiberscope, a camera is attached to the eyepiece of the probe to take a picture of the object to be examined. In this case, underexposure is compensated by a flash light source or the like, and thus an exposure time of 1/125 sec or less must be substantially used.

In an endoscope using a solid-state image pickup device, however, since an image on the TV monitor is photographed as a picture, the display image is normally frozen (i.e., the display image is temporarily processed to obtain a still image). More specifically, a frame memory is arranged in a video processor for processing an image signal, and one-frame image data is stored in the frame memory. The stored image is repeatedly read out to obtain a still image. In order to store a one-frame image in the frame memory, the write time is 1/30 sec corresponding to a two-field period according to the normal interlaced TV scanning.

In a conventional endoscope apparatus using a solid-state image pickup device, since a light pulse is emitted at the start timing of each field period, as previously described, an image of two fields constituting one frame is lagged by time interval (1/60 sec since the one-field period is 1/60 sec) T1 corresponding to the one-field period, i.e., an interval between two pulses for obtaining an image. For this reason, a one-frame still image formed by the two fields during freezing is blurred because of a lapse of time interval T1.

Figures 3A, 3B:
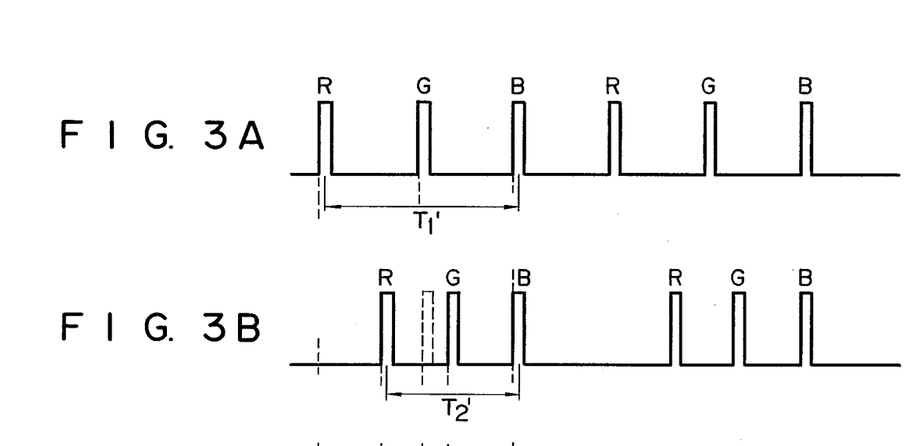
FIGS. 3A to 3D are timing charts for explaining the illumination timings of light pulses according to a conventional field sequential color scheme and a field sequential color scheme of the present invention.
Figure 3C:
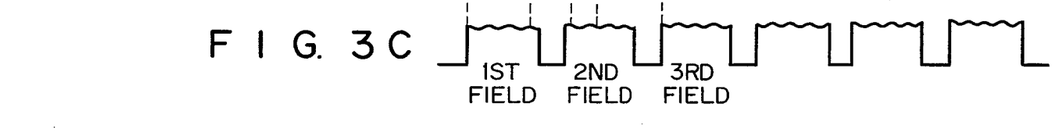
Figure 3D:
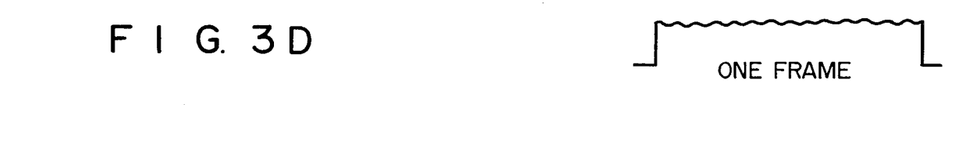

According to still another conventional endoscope apparatus, beams of the three primary colors, i.e., red (R), green (G), and blue (B) are sequentially emitted onto the photographing portion in units of fields. Image data derived by these color components from the solid-state image pickup device is stored in the respective color memories. Output signals from these memories are mixed to obtain a one-frame color image signal. This endoscope apparatus is called a field sequential color image pickup type endoscope apparatus. In this apparatus, if continuous light instead of light pulses is used, the period of three fields (1/20 sec if the one-field period is 1/60 sec) is required to store a signal of three color components, i.e., one frame, in a memory. For this reason, if the image is frozen, a time lag occurs by the differences between the timings of images of the respective color components. It is difficult to obtain a good frozen image for a moving image. As a result, a still image of high quality cannot be recorded. It is also possible to use light pulses in place of continuous light to illuminate the portion to be photographed. As shown in FIGS. 3A, 3C, and 3D, if light pulses are emitted in synchronism with the field period at the start timings of the fields, period T1' (1/30 second if the one-field period is 1/60 sec) substantially corresponding to the two-field period is required to obtain a one-frame image. As a result, a still image of high quality cannot be obtained.

SUMMARY OF THE INVENTION

It is an object of the present invention to provide an endoscope apparatus having a solid-state image pickup device in an insertion portion, wherein "blurring" between fields of the frozen image is minimized to obtain a one-frame still image of good quality.

In an endoscope of the present invention, an object to be picked up is irradiated with light pulses, the pulse timings are set at predetermined regions within the field period, and thus a still image of high quality can be obtained within a minimum period.

According to the present invention, there is therefore provided an endoscope apparatus capable of obtaining a one-frame still image of high quality with little blurring between the fields for the frozen image.

DETAILED DESCRIPTION OF THE PREFERRED EMBODIMENTS

Figure 4:
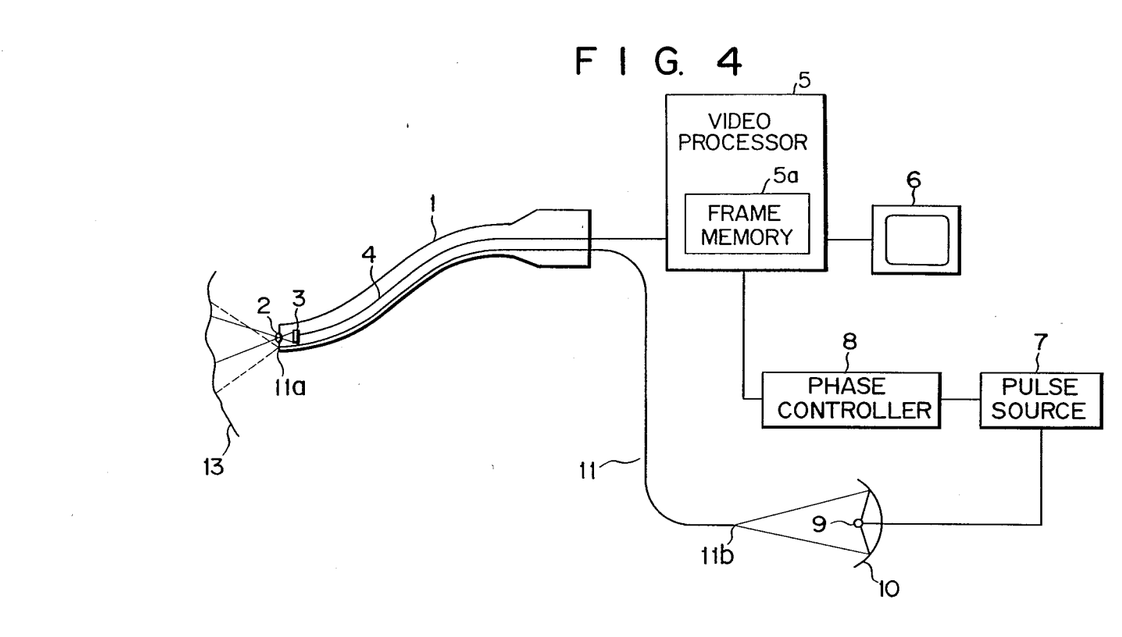
FIG. 4 is a schematic diagram of an endoscope apparatus according to a first embodiment of the present invention.

FIG. 4 shows an overall configuration of an endoscope apparatus according to a first embodiment of the present invention.

The endoscope apparatus in FIG. 4 comprises endoscope insertion portion 1, video processor 5, TV monitor 6, pulse power source 7, pulse phase controller 8, light source 9, mirror 10, and light guide 11. Optical system 2 including an objective lens and solid-state image pickup device 3 consisting of, for example, CCD (Charge-Coupled Device) image pickup device are incorporated in the distal end of insertion portion 1. One end (i.e., an output side) of light guide 11 is located at the distal end of insertion portion 1. Light guide 11 is extracted outside from the proximal end of insertion portion 1 through the interior of insertion portion 1. Light guide 11 is designed to guide light from light source 9 at the other end (i.e., the input side) of guide 11 to the distal end of insertion portion 1 through insertion portion 1, thereby illuminating portion 13 subjected to image pickup.

Video processor 5 comprises a frame memory 5a. Video processor 5 receives an image signal supplied from image pickup device 3 through transmission line 4 and sequentially updates the contents of the frame memory 5a. TV monitor 6 displays an image on the basis of a video signal output from video processor 5. Processor 5 has a moving image mode and a freezing mode. Processor 5 is normally operated in the moving image mode. However, if a freezing instruction is supplied to processor 5, processor 5 is operated in the freezing mode. The freezing instruction is generated by a freeze switch (not shown) turned on by the operator. In the freezing mode, new data is not written in the frame memory 5a and the image data is repeatedly read out as a video signal from the frame memory 5a. In the moving image mode, an output from solid-state image pickup device 3 is output as a video signal without modifications. Alternatively, outputs from image pickup device 3 are sequentially written and updated, so that the storage data is read out from the frame memory 5a.

Pulse power source 7 causes light source 9 of a lamp to generate light pulses. The ON timings of pulse power source 7 are controlled by controller 8 in response to a vertical sync signal from a TV camera control circuit incorporated in processor 5.

Although light pulses are emitted in a conventional endoscope apparatus, as shown in FIG. 2A, adjacent light pulses are emitted at a shortest time interval defining a blanking period (strictly speaking, a transfer period during the blanking period) between the two fields, as shown in FIG. 2B.

In the endoscope apparatus of this embodiment, each frame image is constituted by adjacent (along the time basis) odd and even fields of a video signal as a series of fields obtained by image pickup device 3. In this case, the radiation timings of the light pulses are controlled by pulse phase controller 8. As shown in FIG. 2B, one pulse is generated at the end of a given field period, i.e., the first field period (e.g., an odd field) and one pulse is generated at the start of the next field, that is, the second field (e.g., an even field). The amount of the first light pulse is the same as that of the second light pulse. In this case, the amount of light for compensating a change in brightness caused by a change in distance from the distal end of insertion portion 1 to portion 13 is performed by changing a pulse width.

The light pulses at the end of the first field and the start of the second field may be constituted by a group of narrow pulses each. With this arrangement, the amount of light for each field can be controlled by adjusting the number of pulses. Therefore, light amount control for a change in distance between the distal end of insertion portion 1 and portion 13 can be easily achieved.

Light pulse emission for one frame constituted by the first and second fields can be performed within a shortest interval interposing a blacking period between the fields.

In the normal arrangement of the apparatus, T2/T1 can be set to be 1/13 to 1/15. It is easy to extract a one-frame image within about 1/10 of 1/60 sec as the one-field period. In the freezing mode, the resultant still image is the same as the case wherein an exposure time is set to be 1/600 sec in a still camera, thereby minimizing blurring of the still image. In the freezing mode, when the one-frame image consisting of the first and second fields is written in the frame memory 5a by video processor 5, write access of the memory 5a is interrupted.

An endoscope apparatus according to a second embodiment of the present invention will be described below.

Figure 5:
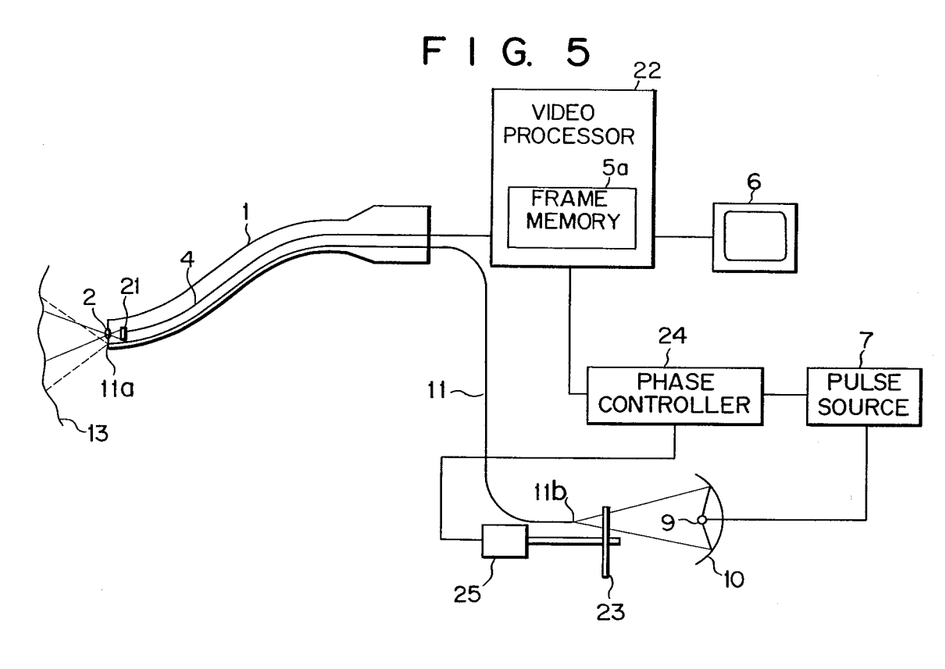
FIG. 5 is a schematic diagram of an endoscope apparatus according to a second embodiment of the present invention.

The same reference numerals as in FIG. 4 denote the same parts in FIG. 5, and a detailed description thereof will be omitted.

Figure 6:
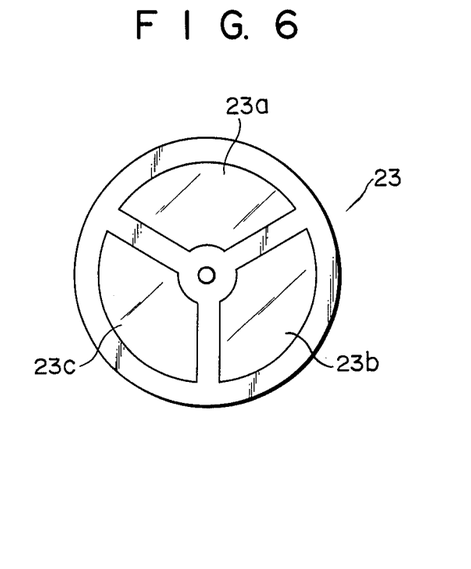
FIG. 6 is a plan view of a filter disc used in the endoscope apparatus in FIG. 5.

An endoscope apparatus in FIG. 5 employs a field sequential color image pickup scheme. Three succeeding field image data derived from light rays of different color components from solid-state image pickup device 21 constitutes a one-frame color image. Therefore, solid-state image pickup device 21 and video processor 22 superpose image data of three fields without performing interlaced scanning to form a one-frame image. Tricolor filter disc 23 is arranged along an optical path between light source 9 and input end 11b of light guide 11. As shown in FIG. 6, filter disc 23 has sector-shaped R (red), G (green), and B (blue) filters 23a, 23b, and 23c. Disc 23 is rotated by motor 25 controlled by pulse phase controller 24. Upon rotation of motor 25 and hence disc 23, R, G and B filters 23a, 23b, and 23c are sequentially inserted in the optical path in synchronism of the radiation color components for each field.

The light pulse emission timings are controlled by phase controller 24, as shown in FIG. 3B. The R component is emitted at the end of the first field, the G component is then emitted at an arbitrary timing within the second field period, and the B component is finally emitted at the end of the third field.

Light pulse radiation for obtaining a one-frame image is completed within shortest period T2' extending through the three-field period constituting the one-frame period. Therefore, the still image is picked up within period T2' slightly exceeding the one-field period. In the case of FIG. 3A, blurring and color misregistration can be greatly reduced as compared with the case of FIG. 3A wherein time interval T1' corresponding to the 2-field period is required.

Even in the embodiment of FIG. 5, blurring and color misregistration occur due to the lapse of time interval T2'. However, the timing of the G component pulse is shifted in consideration of the color of the object subjected to image pickup, thereby eliminating blurring and color misregistration. More specifically, most of the components of an image of a body cavity as a normal object to be picked up by the endoscope apparatus are R and G components. The image of the body cavity includes little B component. As indicated by broken lines in FIG. 3B, the timing of the G light pulse is shifted to the position at the start of the second field period and comes near the timing of the R light pulse. In order to further reduce blurring and color misregistration, the B light pulse may be omitted and only the R and G light pulses are used to form a still image. If the color of the object subjected to image pickup and the three color components for constituting a color image are different from those described above, major two color components are used to form a still image.

An endoscope according to a third embodiment of the present invention will be described hereinafter.

Figure 7:
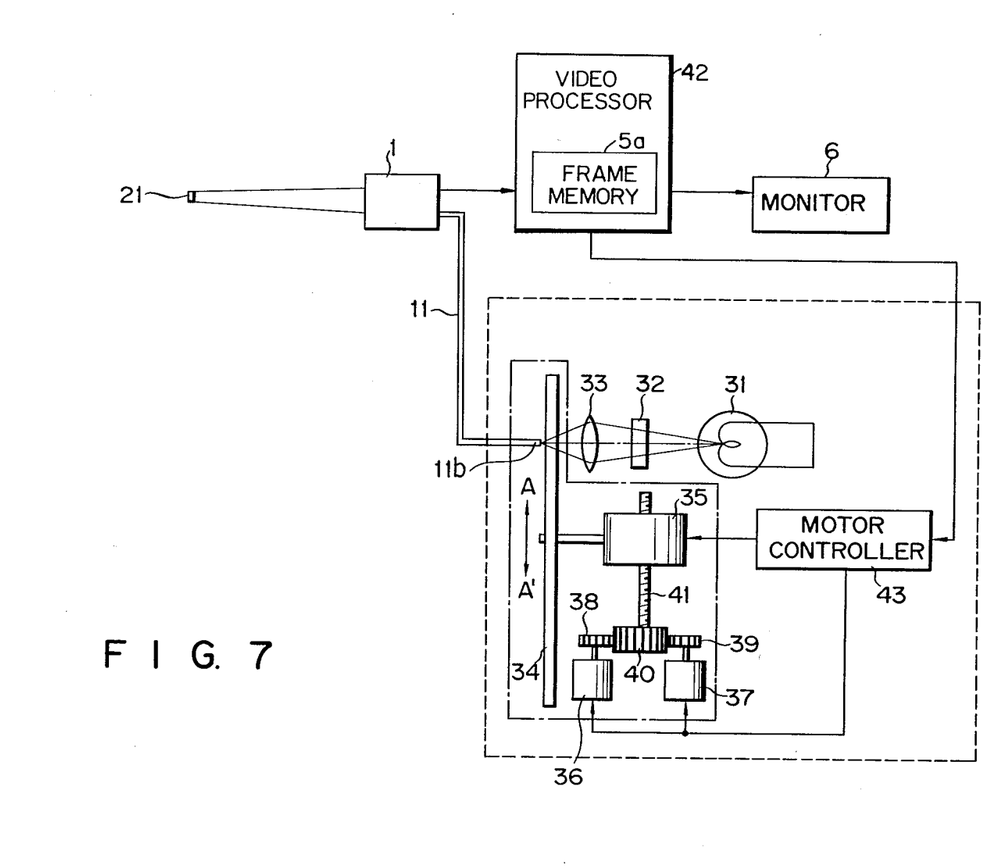
FIG. 7 is a schematic diagram of an endoscope apparatus according to a third embodiment of the present invention.

An overall configuration of the endoscope of the third embodiment is illustrated in FIG. 7. The same reference numerals as in FIG. 4 denote the same parts in FIG. 7.

Continuous white light emitted by light source 31 is incident on condenser lens 33 through infrared absorption filter 32 for eliminating infrared rays (i.e, a heat wave). The white light is focused by lens 33 and incident on input end 11b of light guide 11. Shutter blade 34 is arranged between lens 33 and input end 11b of light guide 11. Blade 34 is rotated by first motor 35 to block an optical path between lens 33 and input end 11b of light guide 11. Motor 35 and shutter blade 34 are shifted in a direction of A—A' by reverse direction drive second and third motors 36 and 37 through gears 38, 39, and 40, and lead screw 41. One-way clutches (not shown) are arranged between gear 38 and motor 36 and between gear 39 and motor 37, respectively. Motor 35 and shutter blade 34 are driven in a direction of A upon operation of one of motors 36 and 37 along one direction and in a direction of A' upon operation of the other of motors 36 and 37. In this case, a single reversible motor may be used to drive lead screw 41 to reciprocate motor 35 and shutter blade 34. The operation of motors 35, 36, and 37 is controlled by motor control circuit 43 responding to video processor 42.

Video processor 42 forms a frame image on the basis of a video signal from solid-state image pickup device 3. Video processor 42 has a function for comparing a detected amount of light from the portion subjected to image pickup with an optical value on the basis of the video signal from image pickup device 3. A light amount control signal corresponding to the discrimination result is supplied together with a frame rate signal of the video signal to motor control circuit 43. Control circuit 43 synchronizes the video frame rate with the speed of first motor 35 for driving shutter blade 34 in response to the video frame rate signal so that the speeds of second and third motors 36 and 37 are controlled in response to the light amount control signal.

Figure 8:
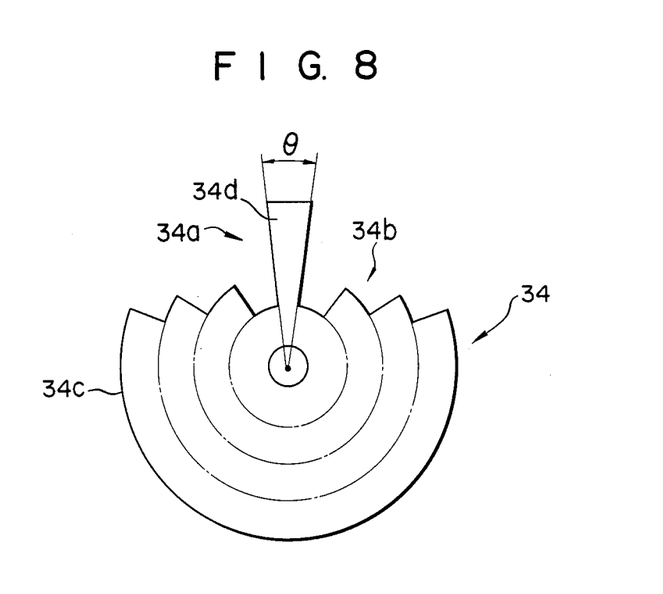
FIG. 8 is a schematic view showing a shutter blade used in the endoscope apparatus of FIG. 7.

In this case, shutter blade 34 intermittently blocks continuous light from light source 31 to generate light pulses. As shown in FIG. 8, shutter blade 34 has first and second exposure openings 34a and 34b of notches. Blade 34 is constituted by first and second light-shielding portions 34c and 34d. Second light-shielding portion 34d has a wedged portion with angle $\theta$. It is desired that angle $\theta$ with respect to 360 degrees is slightly larger than a value corresponding to light nonsensitive time between the fields constituting the frame period, i.e., the value corresponding to the transfer period. Opening angles of opening portions 34a and 34b in first light-shielding portion 34c vary according to diameters thereof. More specifically, the opening angles are increased in three steps when the diameter is increased.

With this arrangement, when shutter blade 34 is rotated at a predetermined angular speed synchronized with the frame rate and intermittently blocks light from light source 31, light pulses shown in FIG. 2B are emitted onto the portion subjected to image pickup. Upon detection of the light amount by video processor 42, shutter blade 34 is shifted with respect to the optical axis so that the opening angle of shutter blade 34 is changed, i.e., the pulse width is changed. As a result, an optimal light amount can be controlled.

Since the light-shielding portions of shutter blade 34 are asymmetrical about the rotational axis, a dynamic balance cannot be achieved if a uniform material is used. In this case, the thickness of a portion with a small mass may be increased, a counterweight may be mounted on the portion with a small mass, or the material of the portion with a small mass can differ from that of other portions. In addition, a shutter blade may be arranged for a transparent plate, and a light-shielding paint may be applied to the light-shielding portion, thus reducing an unbalance of rotation.

Furthermore, opening angles of the pair of exposure openings in a shutter blade may be predetermined regardless of their radii. In this case, if light amount control is required, a light amount control aperture may be arranged on the illumination light path, so that motors 36 and 37, gears 38, 39, and 40, and lead screw 41 in FIG. 7 can be omitted. Instead, an aperture control device controlled by the motor control circuit is required.

The present invention is also applicable to an arrangement wherein an element excluding a CCD is used as a solid-state image pickup device.

The present invention is applicable to an arrangement wherein an image guide is provided in an insertion portion, and the solid-state image pickup device provided on the proximal end picks up the image guided thorough the image guide.

What is claimed is:

1. An endoscope apparatus comprising:
   a solid-state image pickup device mounted in an insertion portion to be inserted in a body cavity, said solid-state image pickup device being adapted to pickup an image of the body cavity so as to form a one-frame image comprising a plurality of fields each of which has associated therewith a corresponding transfer period;
   storage means for storing the one-frame image constituted by an image signal of a plurality of succeeding fields obtained from said solid-state image pickup device;
   display means for displaying the image stored in said storage means; and
   illuminating means for illuminating a portion of said body cavity by emitting a light pulse for each of at least two of said fields in a frame (i) with the light pulse for the first of said two fields in each frame being emitted immediately preceeding the transfer period separating said first of said two fields and the next succeeding field in said frame and (ii) with the light pulse for the other of said two fields in each frame being emitted immediately after the transfer period separating said other field and the immediately preceeding field in said frame.

2. An apparatus according to claim 1, wherein said solid-state image pickup device forms the one-frame image by an image signal of two succeeding fields, and said illuminating means includes means for emitting the light pulses at an end of a first one of the two succeeding fields and at a beginning of a second one of the two succeeding fields.

3. An apparatus according to claim 1, wherein said solid-state image pickup device forms a one-frame color image from an image signal of three succeeding fields, and said illuminating means includes means for emitting the light pulse of a first color at an end of a first one of the three succeeding fields, the light pulse of a second color within a second one of the three succeeding fields, and the light pulse of a third color at a beginning of a third one of the three succeeding fields.

4. An apparatus according to claim 1, wherein said solid-state image pickup device forms a one-frame color image from an image signal of three succeeding fields, and said illuminating means includes means for emitting the light pulses of first to third colors in the three succeeding fields, one of the light pulses of major two colors out of the first to third colors being emitted at an end of a first one of two fields out of the three succeeding fields, and the other of the light pulses of the major two colors being emitted at a beginning of a second one of the two fields out of the three succeeding fields.

5. An apparatus according to claim 1, wherein said plurality of light pulses emitted by said illuminating means each comprise a group of light pulses with narrow widths.

6. An apparatus according to claim 1, wherein said illuminating means includes a light source for emitting light upon reception of electric power, power supplying means for supplying pulsed power to said light source, and phase control means for controlling timings of the pulsed power supplied from said power supplying means.

7. An apparatus according to claim 1, wherein said illuminating means includes a light source for generating continuous light, and light-shielding means for intermittently shielding the continuous light from said light source at predetermined timings in response to synchronization data from said solid-state image pickup device.

8. An apparatus according to claim 7, wherein said light-shielding means includes a rotary light-shielding plate having a plurality of light-transmitting portions at angular positions respectively corresponding to predetermined timings, and rotary driving means for rotating said rotary light-shielding plate at the same period as the field period of said solid-state image pickup device.

9. An apparatus according to claim 8, wherein said rotary light-shielding plate comprises a light-shielding plate having light-transmitting portions each becoming broader or narrower from the center of the plate toward the circumference thereof, and further comprising moving means for changing a relative distance between a rotating shaft of said rotary light-shielding plate and an optical path of the light intermittently shielded by said light-shielding plate.

* * * * *